United States Patent [19]

Berge et al.

[11] Patent Number: 5,310,750
[45] Date of Patent: May 10, 1994

[54] HETEROCYCLIC COMPOUNDS USEFUL AS $\alpha_2$-ADRENOCEPTOR ANTAGONISTS

[75] Inventors: John M. Berge; Michael A. Cawthorne, both of Epsom, England

[73] Assignee: Beecham Group P.L.C., Epsom, England

[21] Appl. No.: 663,393

[22] Filed: Mar. 1, 1991

Related U.S. Application Data

[60] Division of Ser. No. 581,202, Sep. 10, 1990, Pat. No. 5,021,445, which is a continuation of Ser. No. 260,004, Oct. 19, 1988, abandoned.

[30] Foreign Application Priority Data

Oct. 19, 1987 [GB] United Kingdom ........... 8724441
Nov. 9, 1987 [GB] United Kingdom ........... 8726197

[51] Int. Cl.$^5$ ............... A61K 31/415; C07D 401/06; C07D 403/06
[52] U.S. Cl. ............... 514/402; 514/213; 514/307; 514/397; 540/603; 540/594; 546/148; 548/314.7
[58] Field of Search ............ 540/594, 603; 546/148; 548/348, 314.7; 514/213, 307, 402, 397

[56] References Cited

U.S. PATENT DOCUMENTS 4,863,946 9/1989 Berge ................. 548/336

FOREIGN PATENT DOCUMENTS 238753 9/1987 European Pat. Off. .

Primary Examiner—Floyd D. Higel
Attorney, Agent, or Firm—Hopgood, Calimafde, Kalil, Blaustein & Judlowe

[57] ABSTRACT

A compound of formula (I):

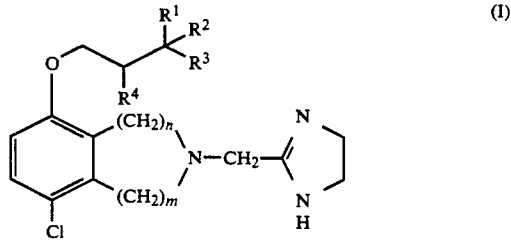

or a pharmaceutically acceptable salt thereof, wherein:
$R^1$ and $R^2$ may each represent hydrogen or alkyl providing that at least one of $R^1$ or $R^2$ represents alkyl;
$R^3$ and $R^4$ each represent hydrogen or $R^3$ and $R^4$ together represent a bond;
n represents an integer 1 or 2;
and m represents an integer 1 or 2; a composition containing such a compound and the method of using such compounds and compositions in medicine.

9 Claims, No Drawings

HETEROCYCLIC COMPOUNDS USEFUL AS α₂-ADRENOCEPTOR ANTAGONISTS

This application is a divisional application of application Ser. No. 07/581,202, filed Sep. 10, 1990, now U.S. Pat. No. 5,021,445, which is a continuation of application Ser. No. 260,004, filed Oct. 19, 1988, now abandoned.

This invention relates to a certain class of heterocyclic compounds having activity as α₂-adrenoceptor antagonists, to a process for preparing such compounds, to pharmaceutical compositions containing such compounds and the use of such compounds and compositions in medicine.

European Patent Application, Publication No. 0238753 discloses certain heterocyclic compounds of the general formula (A):

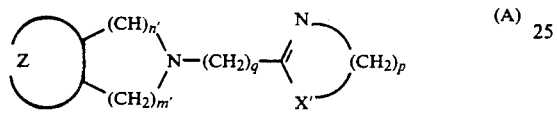

or a pharmaceutically acceptable salt, ester or amide thereof, wherein:

Z represents a residue of a substituted or unsubstituted aryl group,

X' represents O or NR° wherein R° represents a hydrogen atom, a substituted or unsubstituted alkyl group, a substituted or unsubstituted aryl group, an alkanoyl group substituted or unsubstituted in the alkyl moiety, or an arylalkyl moiety substituted or unsubstituted in the aryl moiety, n' represents an integer 1 or 2, m' represents an integer 1 or 2, p represents an integer 2 or 3, and q represents an integer in the range of from 1 to 12.

The compounds of formula (A) are disclosed as having good α₂-adrenoceptor antagonist activity and to be of potential use for the treatment and/or prophylaxis of hyperglycaemia and/or glaucoma and/or the treatment of hypertension and/or depression and/or for inhibiting blood platelet aggregation.

A small class of heterocyclic compounds that fall within the general formula (A) but which are not specifically disclosed in EP 0238753 has now surprisingly been discovered to have very good electivity for the post-junctional α₂-receptor and therefore shows good selectivity from side effects. These compounds are therefore of particular value in the treatment and/or prophylaxis of hyperglycaemia and/or the treatment of hypertension and/or for inhibiting blood platelet aggregation.

Accordingly, the present invention provides a compound of formula (I):

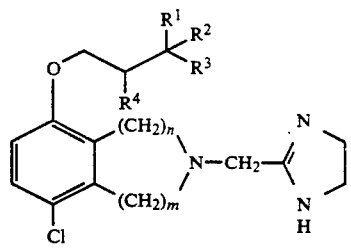

or a pharmaceutically acceptable salt thereof, wherein:

R¹ and R² may each represent hydrogen or alkyl providing that at least one of R¹ and R² represents alkyl;

R³ and R⁴ each represent hydrogen or R³ and R⁴ together represent a bond;

n represents an integer 1 or 2;

and m represents an integer 1 or 2.

Suitably, R¹ and R² each represent alkyl.
Preferably, R¹ and R² each represent methyl.
Suitably, R³ and R⁴ each represent hydrogen.
Suitably, R³ and R⁴ together represent a bond.
Suitably n represents 1.
Suitably m represents 1.

In a preferred aspect the present invention provides a compound selected from the group consisting of:

2(2H-[7-chloro-4-(3-methylbut-2-enyloxy)-1,3-dihydroisoindole]methyl)-4,5-dihydromidazole; and 2-(2H-[7-chloro-4-(3-methylbutyloxy)-1,3-dihydroisoindole]methyl)-4,5-dihydromidazole; or a pharmaceutically acceptable salt thereof.

Suitable pharmaceutically acceptable salts of the compound of formula (I) include acid addition salts.

Suitable pharmaceutically acceptable acid addition salt of compound (I) include pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methane sulphonate, c-ketoglutarate, α-glycerophosphate, and glucose-1-phosphate. Preferably the acid addition salt is a hemisuccinate, hydrochloride, α-ketoglutarate, α-glycerophosphate or glucose-1-phosphate, in particular the hydrochloride salt.

When used herein the term 'alkyl' includes straight and branched chain alkyl groups containing from 1 to 12 carbon atoms, suitably 1 to 6 carbon atoms, such as methyl, ethyl, propyl and butyl groups.

The present invention also provides a process for the preparation of a compound of formula (I), or a pharmaceutically acceptable salt thereof, which process comprises cyclising a compound of formula (II):

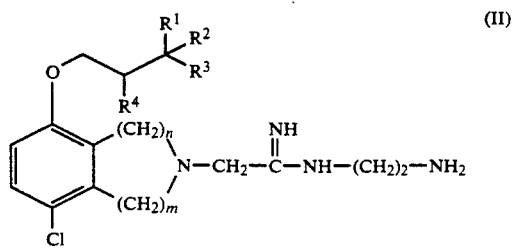

wherein $R^1$, $R^2$, $R^3$, $R^4$, m and n are as defined in relation to formula (I); and thereafter, if required, converting a compound of formula (I) into a further compound of formula (I) and/or forming a pharmaceutically acceptable salt thereof. A compound of formula (II) may be prepared by reacting a compound of formula (III):

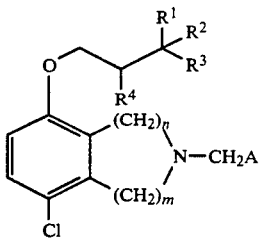 (III)

wherein $R^1$, $R^2$, $R^3$, $R^4$, m and n are as defined in relation to formula (I) and A represents —CN or —$CO_2R$ wherein R represents $C_{1-6}$ alkyl, with 1,2-diaminoethane or an activated form thereof.

A suitable activated form of 1,2-diaminoethane is the trimethylaluminium adduct of 1,2-diaminoethane. The activated form of 1,2-diaminoethane is generally the preferred reagent when A represents —$CO_2R$.

Suitably, R represents methyl.

A compound of formula (III) may be prepared by reacting a compound of formula (IV):

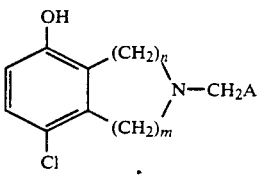 (IV)

wherein m and n are as defined in relation to formula (I) and A is as defined in relation to formula (III), with a compound of formula (V):

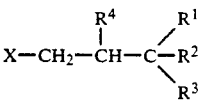 (V)

wherein $R^1$, $R^2$, $R^3$ and $R^4$ are as defined in relation to formula (I) and X represents a leaving group, preferably a bromine atom.

The compounds of formula (V) are known compounds or they may be prepared using methods analogous to those used to prepare known compounds.

A compound of formula (IV) may be prepared by reacting a compound of formula (VI):

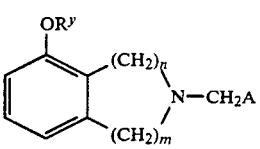 (VI)

wherein m and n are as defined in relation to formula (I) and A is as defined in relation to formula (III) and $R^y$ represents a hydroxyl protecting group, with a chlorinating agent, and thereafter removing the protecting group $R^y$.

A suitable chlorinating agent is any agent capable of inserting a chlorine atom in the required position on the phenyl group of the compound of formula (VI) without affecting the rest of the molecule.

Conveniently, sulphuryl chloride may be used as the chlorinating agent.

A compound of formula (VI) may be prepared by reacting a compound of formula (VII):

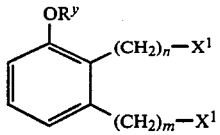 (VII)

wherein m, n and Ry are as defined in relation to formula (VI) and $X^1$ represents a leaving group, with a compound of formula (VIII):

$H_2N—CH_2—A$ (VIII)

wherein A is as defined in relation to formula (III), and thereafter, if required, converting a compound of formula (VI) into another compound of formula (VI).

Suitably, $X^1$ represents a halogen atom, especially a chlorine or bromine atom, a methanesulphonate group or a p-toluenesulphonate group.

Preferably $X^1$ represents a bromine atom.

Suitable conversions of one compound of formula (VI) into another compound of formula (VI) include those wherein A, in formula (VI), is converted from one value into another value: for example a compound of formula (VI) wherein A represents nitrile may be converted into a compound of formula (VI) wherein A represents —$CO_2R$, wherein R is as defined in relation to formula (III), by any conventional procedure, for example by hydrolysis to give the corresponding carboxylic acid followed by esterification.

Suitable conditions for hydrolysing, the nitrile group include acid conditions, for example using aqueous hydrobromic acid.

Suitable conditions for esterification are well known in the art and include treatment with the appropriate alcohol under acidic conditions.

A compound of formula (VII) may be prepared by reaction of a compound of formula (IX):

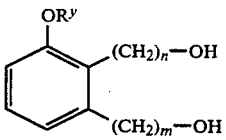 (IX)

wherein m, n and $R^y$ are as defined in relation to formula (VI), with a reagent capable of converting a moiety —$CH_2$—OH into a moiety —$CH_2$—$X^1$.

When $X^1$ represents a halogen atom, especially a chlorine or bromine atom, a suitable reagent is a halogenating agent such as a phosphorous trihalide.

When $X^1$ is chlorine a preferred reagent is phosphorous trichloride.

When $X^1$ is bromine a preferred reagent is phosphorous tribromide.

When $X^1$ represent a methanesulphonate group, a suitable reagent is a methanesulphonyl halide especially methanesulphonyl chloride.

When $X^1$ represents a p-toluenesulphonate group, a suitable reagent is a p-toluenesulphonyl halide especially p-toluenesulphonyl chloride.

A compound of formula (IX) may be prepared by reducing a compound of formula (X):

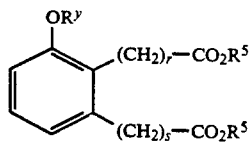

wherein $R^y$ is as defined in relation to formula (VI), r and s each represent either zero or 1 and $R^5$ is a $C_{1-6}$ alkyl group.

A suitable reducing agent is a complex metal hydride such as lithium aluminium hydride.

A compound of formula (X) may be prepared from a compound of formula (XI):

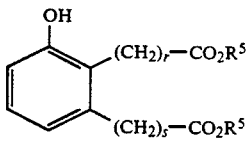

wherein $R^5$, r and s are as defined in relation to formula (X), by converting the hydroxy group therein into a protected hydroxyl group —$OR^y$.

Suitably, $R^5$ is a methyl group.

Suitably, r and s both represent zero.

The compounds of formula (XI) are known compounds or they may be prepared using methods analogous to those used to prepare known compounds, for example those disclosed in Helv. Chim. Acta (1931), 14, 511.

Suitable conversions of one compound of formula (I) into another compound of formula (I) include those in which a compound wherein $R^3$ and $R^4$ together represent a bond is coverted into a compound wherein $R^3$ and $R^4$ each represent hydrogen; such a convension may be carried out using any conventional procedure such as catalytic reduction.

The salts of the compounds of formula (I) may be prepared by the appropriate conventional procedure.

The cyclisation of compounds of formula (II) may be carried out under any appropriate conditions, using any suitable solvent system and temperature range appropriate to the particular compound of formula (II), but usually at an elevated temperature.

Favourably, for the preparation of a compound of formula (I), the compound of formula (II) is not isolated from the reaction between the appropriate compound of formula (III) and 1,2-diaminoethane or an activated form thereof, thus the compound of formula (II) is converted in-situ to a compound of formula (I).

Thus, in this favoured form of the process for the preparation of compounds of formula (I), the appropriate compound of formula (III) and 1,2-diaminoethane are reacted together at an elevated temperature, for example within the range 80° C. to 130° C., preferably 110° C., in any suitable solvent such as toluene; favourably for reactions involving 1,2-diaminoethane the reaction is carried out using 1,2-diaminoethane as solvent; preferably the reaction is carried out in the presence of a catalytic amount of carbon disulphide; preferably the reaction is carried out under an atmosphere of nitrogen.

It will be understood that under the abovementioned conditions the compound of formula (II) initially formed in the reaction between the compound of formula (III) and 1,2-diaminoethane or an activated form thereof; subsequently undergoes cyclisation to give the required compound of formula (I).

Accordingly, in an alternative aspect the present invention provides a process for the preparation of a compound of formula (I) which process comprises reacting a compound of formula (III) with 1,2-diaminoethane and thereafter if required converting a compound of formula (I) into a pharmaceutically acceptable salt thereof.

The reaction between compounds of formulae (IV) and (V) may be carried out in any suitable solvent such as a lower alkyl ketone, for example butanone, at any convenient temperature, suitably at the reflux temperature of the solvent, in the presence of a base, preferably potassium carbonate.

The reaction between the compounds of formula (VI) and the chlorinating agent may be carried out under conditions appropriate to the nature of the chlorinating agent. Thus, for example when the chlorinating agent is sulphuryl chloride, the reaction may conveniently be carried out in any suitable solvent, such as dichloromethane or acetic acid, at a low to ambient temperature, conveniently at ambient temperature.

A compound of formula (VII) may be prepared from a compound of formula (IX) by using conditions appropriate to the nature of the reagent capable of converting a moiety —$CH_2$—OH into a moiety —$CH_2$—$X^1$, for example:

(i) when $X^1$ represents halogen, especially a chlorine or bromine atom and the reagent is a phosphorus trihalide, the reaction may conveniently be carried out at low to ambient temperature, for example at 5° C., in any suitable solvent, such as diethyl ether;

(ii) when $X^1$ represents a methanesulphonate group or a p-toluenesulphonate and the reagent is a methanesulphonyl halide or a toluenesulphonyl halide respectively, the reaction may be carried out in any suitable solvent, such as pyridine, at a low to ambient temperature, suitably at ambient temperature.

The reaction between the compounds of formulae (VII) v and (VIII) may conveniently be carried out in an aprotic solvent, such as dimethylformamide, preferably at a slightly elevated temperature, for example at a temperature in the range of between 20° C. and 60° C.

The reduction of the compound of formula (X) is carried out under conditions appropriate to the reducing agent used. Thus, when lithium aluminium hydride is the reducing agent, the reaction may conveniently be carried out in an aprotic solvent, such as diethyl ether, at low to elevated temperature, more usually at the reflux temperature of the solvent.

In the abovementioned processes any reactive groups may be present as protecting groups. Suitable protecting groups are those used conventionally in the art; for example a suitable hydroxyl protecting group $R^y$ is a benzyl group.

The conditions of preparation and removal of the relevant protecting group are those used conveniently in the art. Thus, when $R^y$ is a benzyl group, the compound of formula (XI) may conveniently be reacted with benzyl bromide in the presence of a base such as potassium carbonate, in a solvent such as dimethylformamide, conveniently at an elevated temperature, for example 80° C. Also, when Ry is a benzyl group the benzyl group may be removed by using a reagent such as boron trifluoride dimethylsulphide complex.

The present invention also provides a compound of formula (I), or a pharmaceutically acceptable salt thereof, for use as an active therapeutic substance.

In a particular aspect, the present invention provides a compound of formula (I), or a pharmaceutically acceptable salt thereof, for use in the treatment and/or prophylaxis of hyperglycaemia.

In a further aspect the present invention provides a compound of formula (I), or a pharmaceutically acceptable salt thereof, for inhibiting blood platelet aggregation.

In a further aspect, the present invention provides a compound of the general formula (I), or a pharmaceutically acceptable salt thereof, for use in the treatment of hypertension in human or non-human mammals.

A compound of the general formula (I), or a pharmaceutically acceptable salt thereof, may be administered per se or, preferably, as a pharmaceutical composition also comprising a pharmaceutically acceptable carrier.

Accordingly, the present invention also provides a pharmaceutical composition comprising a compound of the general formula (I), or a pharmaceutically acceptable salt thereof, and a pharmaceutically acceptable carrier therefor.

As used herein the term "pharmaceutically acceptable" embraces compounds, compositions and ingredients for both human and veterinary use: for example the term "pharmaceutically acceptable salt" embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption, are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, such as Harry's Cosmeticology published by Leonard Hill Books, Remington's Pharmaceutical Sciences, and the British and US Pharmacopoeias.

The compositions of the present invention may be prepared using any conventional process, for example those disclosed in the abovementioned reference texts.

Most suitably the composition will be formulated i unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of formula (I), or a pharmaceutically acceptable salt thereof, to a hyperglycaemic human or non-human mammal in need thereof.

The present invention further provides a method for the treatment of hypertension in a human or non-human mammal, which comprises administering an effective, non-toxic, amount of a compound of formula (I), or a pharmaceutically acceptable salt thereof, to an hypertensive human or non-human mammal.

The invention also provides a method for inhibiting blood platelet aggregation in a human or non-human mammal, which method comprises administering an effective non-toxic amount of a compound of formula (I), or a pharmaceutically acceptable salt thereof, to a human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans or the treatment of hypertensive humans the compound of the formula (I), or a pharmaceutically acceptable salt thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg.

In the inhibition of platelet aggregation in human or non-human mammals, dosage regimes are as indicated above for the treatment and/or prophylaxis of hyperglycaemic human or non-human mammals.

The present invention also provides the use of a compound of formula (I), or a pharmaceutically acceptable salt thereof, for the manufacture of a medicament for the treatment and/or prophylaxis of hyperglycaemia.

The present invention further provides the use of a compound of formula (I) or a pharmaceutically acceptable salt thereof, for the manufacture of a medicament for the inhibition of blood platelet aggregation and/or the treatment of hypertension.

No toxicological effects are indicated when a compound of formula (I), or a pharmaceutically acceptable salt thereof, is administered in any of the abovementioned dosage ranges.

The following Examples illustrate the invention but do not limit it in any way.

EXAMPLE 1

2-(2H-[7-Chloro-4-(3-methylbut-2-enyloxy)-1,3-dihydroisoindole]methyl)-4,5-dihydroimidazole

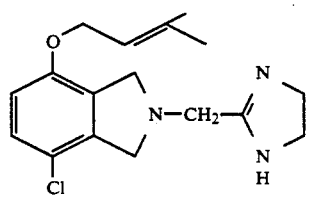

A mixture of 1.0 g (3.6 mmol) of 2H-[7-Chloro-4-(3-methylbut-2-enyloxy)-1,3-dihydroisoindole]acetonitrile, 1 ml (14.9 mmol) of 1,2-diaminoethane and 5 drops of carbon disulphide was heated at 110° C. under an atmosphere of nitrogen. After 6 hours the mixture was cooled and partitioned between dichloromethane and water. The or9anic layer was separated, dried and evaporated to yield the crude product.

Recrystallisation from ethyl acetate gave the title compound as an off white solid.

1H-nmr δ (CDCl₃):

7.10 (1H,d); 6.66 (1H,d); 5.42 (1H,t); 4.49 (2H,d); 4.03 (4H,s); 3.7–3.5 (1H,broad signal, exchanges with D₂O); 3.65 (4H,s); 3.55 (2H,s); 1.78 (3H,s); 1.72 (3H,s).

EXAMPLE 2

2-(2H-[7-Chloro-4-(3-methylbutyloxy)-1,3-dihydroisoindole]methyl)-4 5-dihydroimidazole

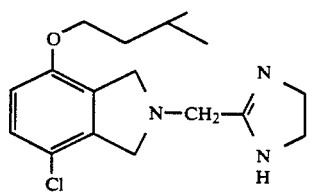

The title compound, mp. 128°–129°, was obtained from 1.0 g (3.59 mmole) of 2H-[7-chloro-4-(3-methylbutyloxy)-1,3-dihydroisoindole)acetonitrile and 1 ml (14.9 mmole) of 1,2-diaminoethane by an analogous procedure to that described in Example 1.

¹H-nmr δ (CDCl₃+D₂O):

7.12 (1H, d); 6.66 (1H, d); 4.02 (4H, s); 3.98 (1H, d); 3.96 (1H, d); 3.65 (4H, s); 3.59 (2H, s); 1.9-1.7 (1H, m); 1.66 (1H, d); 1.63 (1H, d); 0.95 (6H, d).

Procedure 1

Dimethyl 3-benzyloxyphthalate

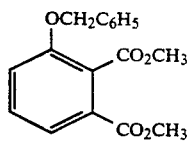

A mixture of 14.5 g (69 mmol) of dimethyl 3-hydroxyphthalate, 9.6 g (69 mmol) of anhydrous potassium carbonate and 8.23 ml (69 mmol) of benzyl bromide in 50 ml of dry dimethylformamide was heated with stirring at 80° C.

After 18 hours the mixture was cooled and poured into 500 ml of water, and extracted into diethyl ether 3×100 ml). The combined organic extracts were dried and evaporated to yield the crude compound as an oil. Chromatography over silica gel eluting with hexane/diethyl ether (0→50%) gave the title compound as an oil.

1H-nmr δ (CDCl₃):

7.7–7.0 (8H,m); 5.14 (2H,s); 3.90 (3H,s); 3.78 (3H,s).

Procedure 2

3-Benzyloxy-1,2-bishydroxymethylbenzene

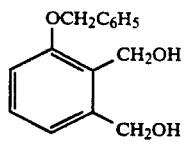

To a suspension Of 10 g Of lithium aluminium hydride in 300 ml of dry diethyl ether was added dropwise a solution of 18 g (60 mmol) of dimethyl 3-benzyloxy phthalate in 125 ml of dry diethyl ether.

After heating under reflux for 4 hours the mixture was cooled and treated sequentially with 10 ml of water, 10 ml of 10% sodium hydroxide solution and 20 ml of water. The resultant mixture was filtered and the filtrate evaporated to yield the title compound as a pale yellow oil.

¹H-nmr δ (CDCl₃):

7.6–7.1 (6H,m); 7.0-6.8 (2H,m); 5.04 (2H,s); 4.76 (2H,s); 4.55 (2H,s); 3.8–3.3 (2H,broad signal, exchanges with D₂O).

Procedure 3

3-Benzyloxy-1,2-bisbromomethylbenzene

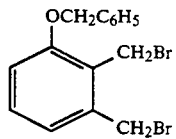

To a solution of 12 g (49.2 mmol) of 3-benzyloxy-1,2-bishydroxymethylbenzene in 350 ml of dry diethyl ether at 5° C. was added dropwise 30 ml (252 mmol) of phosphorus tribromide in 50 ml of dry diethyl ether. After stirring at room temperature for 14 hours the mixture was poured onto 500 g of ice, the organic layer was separated, washed with 200 ml of water, 200 ml of saturated sodium bicarbonate solution and 200 ml of brine. Drying and evaporation of the resultant organic phase gave the title compound as a white solid.

¹H-nmr δ (CDCl₃):

7.7–7.1 (6H,m); 7.1-6.9 (2H,m); 5.17 (2H,s); 4.86 (2H,s); 4.65 (2H,s).

Procedure 4

2H-(4-Benzyloxy-1,3-dihydroisoindole)acetonitrile

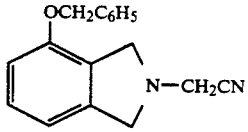

To a mixture of 5.14 g (55.5 mmol) of aminoacetonitrile hydrochloride and 18.3 ml (134 mmol) of triethylamine in 75 ml of dry dimethylformamide at 50° C. was added dropwise a solution of 15 g (40.5 mmol) of 3-benzyloxy-1,2- bisbromomethylbenzene in 50 ml of dry dimethylformamide. The temperature was maintained at 50° C. for 3 hours. After stirring at room temperature for 14 hours the mixture was poured into 500 ml of water. The resultant aqueous phase was extracted three times with 150 ml portions of diethyl ether. The combined organic layers were dried and evaporated to yield a pale yellow oil.

$^1$H-nmr (CDCl$_3$):

7.5–6.6 (8H,m); 5.00 (2H,s); 4.03 (4H,s); 3.68 (2H,s)

Procedure 5

2H-(4-Benzyloxy-7-chloro-1,3-dihydroisoindole)acetonitrile

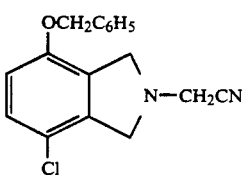

To a solution of 6.9 g (26.1 mmol) of 2H-(3-benzloxy-1,3-dihydroisoindole)acetonitrile in 70 ml of dichloromethane at room temperature was added 2.1 ml (26.1 mmol) of sulphuryl chloride. After stirring for 0.5 hours a further 2.1 ml of sulphuryl chloride was added. The mixture was stirred for 1 hour after which the solvent was evaporated. The resultant mixture was partitioned between saturated sodium bicarbonate solution and dichloromethane. The organic phase was separated, dried and evaporated to yield the crude product. Chromatography over silica gel, eluting with dichloromethane, gave the title compound as a pale yellow oil.

$^1$H-nmr δ (CDCl$_3$):

7.5–7.1 (5H,m); 7.01 (1H,d); 6.50 (1H,d); 4.88 (2H,s) 4.02 (4H,s); 3.65 (2H,s).

Procedure 6

2H-(7-Chloro-4-hydroxy-1.3-dihydroisoindole)acetonitrile

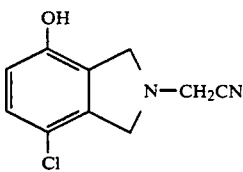

To a solution of 3.2 g (10.7 mmol) of 2H-(4-benzloxy-7-chloro-1,3-dihydroisoindole)acetonitrile in 40 ml of dichloromethane at room temperature, under an atmosphere of nitrogen, was added 15.6 ml (120 mmol) of boron trifluoride dimethylsulphide complex. After stirring for 3 hours the mixture was poured into water. The resultant aqueous phase was neutralised with solid sodium bicarbonate and extracted (4 x 100 ml aliquots) with dichloromethane. The combined organic extracts were dried and evaporated to yield the crude product. Chromatography over silica gel, eluting with dichloromethane/methanol (0→2%), gave the title compound.

$^1$H-nmr δ (CDCl$_3$):

6.95 (1H,d); 6.60 (1H,s exchanges with D$_2$O); 6.48 (1H,d); 4.05 (4H,s); 3.73 (2H,s).

Procedure 7

2H-[7-Chloro-4-(3-methylbut-2-enyloxy)-1,3-dihydroisoindole]acetonitrile

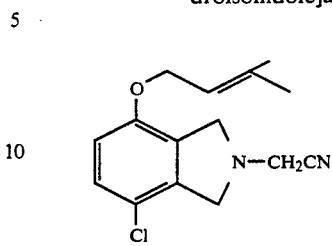

A mixture of 0.8 g (3.8 mmol) of 2H-(7-chloro-4-hydroxy-1,3-dihydroisoindole)acetonitrile and 1.0 g (7.2 mmol) of anhydrous potassium carbonate in 20 ml of butanone was heated under reflux with stirring for 1 hour. The mixture was cooled to room temperature and 0.62 g (3.8 mmol) of 90% 1-bromo-3-methylbut-2-ene was added. Heating was recommenced and continued for 16 hours after which time the mixture was cooled and evaporated to dryness. The residue was partitioned between dichloromethane and water, the organic layer was separated and dried to yield the title compound as an oil.

$^1$H-nmr δ (CDCl$_3$):

7.10 (1H,d); 6.67 (1H,d); 5.42 (1H,t); 4.50 (2H,d); 4.03 (4H,s); 3.68 (2H,s); 1.80 (3H,s); 1.76 (3H,s).

Procedure 8

2H-[7-Chloro-4-(3-methylbutyloxy)-1,3-dihydroisoindole]acetonitrile.

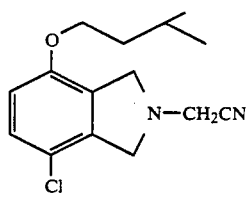

2H-(7-Chloro-4-hydroxy-1,3-dihydroisoindole) acetonitrile, 2.12 g (8.65 mmol) in 25 ml of dry dimethylformamide (DMF) was added to a suspension of 0.69 g (17.25 mmole) of 60% sodium hydride in 10 ml of DMF. After stirring at room temperature for 0.25 h and cooling to 5° C., 1-bromo-3- methylbutane, 1 ml (8.35 mmol), in 5 ml of DMF was added. The reaction mixture was stirred overnight at room temperature, poured into 100 ml of water and then extracted twice, each time with 100 ml portions of diethyl ether. The organic layer was dried and evaporated to yield the title compound as a light brown oil.

$^1$H-nmr δ (CDCl$_3$):

7.12 (1H, d); 6.66 (1H, d); 4.11 (4H, s); 4.0-3.9 (2H, m); 3.75 (2H, s); 2.0-1.5 (3H, m); 0.94 (6H, d).

Pharmacological Data

Demonstration of the Pharmacological Selectivity for Pre- and Post-junctional α$_2$-Adrenoceptors.

To determine post-junctional α$_2$-adrenoceptor activity, ring segments of rabbit lateral saphenous vein were mounted in organ baths at 37° C. containing Krebs medium. Contractions of this tissue in response to noradrenaline are mediated via post-junctional α$_2$- adrenoceptors (Alabaster et al, 1985) and therefore the ability of $\alpha_2$-adrenoceptor antagonists to pharmacologically antagonise such contractions gives a quantitive measure of the activity of compounds for this receptor subtype.

Pre-junctional activity is estimated by the ability of $\alpha_2$-adrenoceptor antagonists to reverse a clonidine-induced inhibition of [$^3$H]-noradrenaline release from segments of rabbit aorta. Rings of rabbit abdominal aorta were incubated at 37° C. in Krebs medium containing 40 $\mu$Ci of [$^3$H]-noradrenaline (specific activity 10–30Ci/mmol) for 1 hour. Tissues were then mounted vertically between parallel platinum electrodes and superfused with tritium-free Krebs medium. Electrical stimulation was carried out using square wave pulses of 0.5 msec duration and 100 V were delivered to the tissues at a frequency of 2 Hz. The superfusate was collected in 3 minute fractions. Six stimuli ($S_1$–$S_6$) were applied to each tissue. Clonidine was added to the superfusion stream after $S_2$ at a concentration of 0.01 $\mu$M and again after $S_3$ at a concentration of 0.1 $\mu$M. Each antagonist added after $S_4$ and a further concentration of clonidine (1 $\mu$M) infused after $S_5$. At the end of each experiment each aortic segment solubilised in 150 $\mu$l of Fisosolve$^R$ tissue solubiliser and the radioactivity of both superfusate samples and aortic rings determined by liquid scintillation spectroscopy.

Results are calculated by the method of Docherty et al. 1982, with stimulation evoked overflow of tritium expressed as a percentage of the tritium content of the tissue at the onset of the respective stimulation period.

| Example Number | Post-synaptic $PA_2$ | Pre-synaptic $PA_2$ |
|---|---|---|
| 1 | 6.6 | <5.0 |
| 2 | 6.7 | 5.4 |

Alabaster V. A., Keir R. F. and Peters C. J. (1985) Naunun-Schmiedeberg's Arch Pharmacol 330, 33–36.
Docherty J. R., Gothert M., Dieckhoffer C. and Starke K. (1982) Arzneim-Forsch, Drug Res., 32, 1534–1540.

We claim:
1. A compound of formula (I):

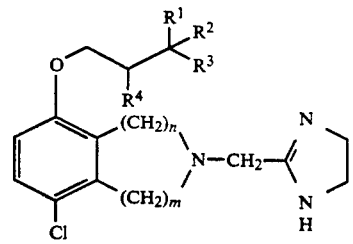

or a pharmaceutically acceptable salt thereof, wherein:
  $R^1$ and $R^2$ may each represent hydrogen or $C_{1-12}$ alkyl providing that at least one of $R^1$ and $R^2$ represents alkyl;
  $R^3$ and $R^4$ each represent hydrogen;
  and m and n are equal to each other and represent an integer 1 or 2.

2. A compound according to claim 1, wherein $R^1$ and $R^2$ each represent alkyl.

3. A compound according to claim 1, wherein $R^1$ and $R^2$ each represent methyl.

4. A compound according to claim 1, wherein n represents 1.

5. A compound according to claim 1, wherein m represents 1.

6. A compound according to claim 1 which is 2-(2H-[7-chloro-4-(3-methylbutyloxy)-1,3-dihydroisoindole]-methyl)-4,5-dihydroimidazole or a pharmaceutically acceptable salt thereof.

7. A pharmaceutical composition for use as an alpha-2-adrenoreceptor antagonist which comprises a pharmaceutically effective amount of a compound of formula (I) as defined by claim 1, or a pharmaceutically acceptable salt thereof, and a pharmaceutically acceptable carrier therefor.

8. A method for the treatment of hyperglycaemia in a human or non-human mammal which comprises administering an effective, non-toxic, amount of a compound of formula (I) as recited in claim 1, or a pharmaceutically acceptable salt thereof, to a hyperglycaemic human or non-human mammal in need thereof.

9. A method for the treatment and/or prophylaxis of hypertension and/or inhibiting blood platelet aggregation in a human or non-human mammal, which method comprises administering an effective non-toxic amount of a compound of formula (I) as recited in claim 1, or a pharmaceutically acceptable salt thereof, to a human or non-human mammal in need thereof.

* * * * *